(12) United States Patent
Gerber et al.

(10) Patent No.: US 7,623,923 B2
(45) Date of Patent: *Nov. 24, 2009

(54) TUBE SENSOR FOR PENILE TUMESCENCE

(75) Inventors: Martin T. Gerber, Maple Grove, MN (US); Keith A. Miesel, St. Paul, MN (US)

(73) Assignee: Medtronic, Inc., Minneapolis, MN (US)

(*) Notice: Subject to any disclaimer, the term of this patent is extended or adjusted under 35 U.S.C. 154(b) by 230 days.

This patent is subject to a terminal disclaimer.

(21) Appl. No.: 11/117,054

(22) Filed: Apr. 28, 2005

(65) Prior Publication Data

US 2006/0247682 A1 Nov. 2, 2006

(51) Int. Cl.
*A61N 1/08* (2006.01)
*A61F 5/41* (2006.01)

(52) U.S. Cl. ........................................ 607/39; 607/143

(58) Field of Classification Search ................. 607/115, 607/138, 142, 143, 39, 40, 41; 600/38–41
See application file for complete search history.

(56) References Cited

U.S. PATENT DOCUMENTS

| RE33,360 | E  | 10/1990 | Reynolds et al. |
|----------|----|---------|-----------------|
| 5,103,835 | A  | 4/1992 | Yamada et al. |
| 5,134,281 | A  | 7/1992 | Bryenton et al. |
| 5,396,897 | A  | 3/1995 | Jain et al. |
| 6,015,393 | A  | 1/2000 | Hovland et al. |
| 6,162,188 | A  | 12/2000 | Barnea |
| 6,354,991 | B1 | 3/2002 | Gross et al. |
| 6,360,123 | B1 | 3/2002 | Kimchi et al. |
| 6,393,323 | B1 | 5/2002 | Sawan et al. |
| 6,652,449 | B1 | 11/2003 | Gross et al. |
| 6,689,056 | B1 | 2/2004 | Kilcoyne et al. |

(Continued)

FOREIGN PATENT DOCUMENTS

EP 0 694 284 A1 1/1996

(Continued)

OTHER PUBLICATIONS

Coosemans et al., "Datalogger for Bladder Pressure Monitoring with Wireless Power and Data Transmission," Katholieke Universiteit Leuven, Department ESAT-MICAS, Belgium, 1 pg. (Oct. 17, 2003).

(Continued)

*Primary Examiner*—Carl H. Layno
*Assistant Examiner*—Tammie K. Heller
(74) *Attorney, Agent, or Firm*—Shumaker & Sieffert, P.A.

(57) ABSTRACT

The disclosure describes a tube pressure sensor to measure penile tumescence which may be used in a therapeutic penile tumescence control system. The system senses penile pressure and sends the information to a stimulator that is capable of stimulation therapy to control an erectile state, thus treating sexual dysfunction or, more specifically, erectile dysfunction. Measuring penile tumescence pressure is accomplished through the use of a tube placed within the urethra of the penis and attached to a module implanted within the bladder. Pressure on the tube generates an electrical signal that is sent wirelessly to an implanted stimulator connected to a lead positioned near pelvic floor nerves that stimulate erections. An external device may be used to wirelessly send information to the implanted stimulator to start or stop stimulation in order for the patient to conduct normal sexual activity. In addition, pressure information and stimulation information may be recorded and reviewed by a physician for continued therapy monitoring.

22 Claims, 10 Drawing Sheets

U.S. PATENT DOCUMENTS

| | | | |
|---|---|---|---|
| 2002/0055761 A1 | 5/2002 | Mann et al. | |
| 2002/0062060 A1 | 5/2002 | Gross et al. | |
| 2002/0103424 A1 | 8/2002 | Swoyer et al. | |
| 2002/0111586 A1 | 8/2002 | Mosel et al. | |
| 2003/0100929 A1* | 5/2003 | Forsell | 607/39 |
| 2003/0100930 A1 | 5/2003 | Cohen et al. | |
| 2003/0220292 A1 | 11/2003 | Okada et al. | |
| 2003/0236557 A1 | 12/2003 | Whitehurst et al. | |
| 2003/0236558 A1 | 12/2003 | Whitehurst et al. | |
| 2004/0015204 A1 | 1/2004 | Whitehurst et al. | |
| 2004/0015205 A1 | 1/2004 | Whitehurst et al. | |
| 2004/0147871 A1 | 7/2004 | Burnett | |
| 2004/0152999 A1 | 8/2004 | Cohen et al. | |
| 2005/0065408 A1 | 3/2005 | Benderev | |
| 2005/0245840 A1 | 11/2005 | Christopherson et al. | |
| 2005/0288603 A1 | 12/2005 | Goping | |

OTHER PUBLICATIONS

Siwapornsathain et al., "A Telemetry and Sensor Platform for Ambulatory Urodynamics," Department of Electrical and Computer Engineering, University of Wisconsin, Madison, WI, 5 pgs. (2002).

Van Waalwijk van Doorn, "Standardisation of Ambulatory Urodynamic Monitoring," Report of the Standarisation Sub-committee of the ICS ambulatory urodynamic studies, 21 pgs. (2000).

"Wireless Physiological Pressure Transducer," MEMSCAP Sensor Solutions, 2 pgs. (May 2003).

U.S. Patent Application entitled "Implantable Optical Pressure Sensor for Sensing Urinary Sphincter Pressure", U.S. Appl. No. 11/117,064, filed Apr. 28, 2005.

U.S. Patent Application entitled "Multi-Tube Sensor for Sensing Urinary Sphincter and Urethral Pressure", U.S. Appl. No. 11/117,079, filed Apr. 28, 2005.

U.S. Patent Application entitled "Flexible Tube Sensor for Sensing Urinary Sphincter Pressure", U.S. Appl. No. 11/116,952, filed Apr. 28, 2005.

Responsive Amendment dated Oct. 14, 2008 for U.S. Appl. No. 11/116,952 (11 pgs.).

Office Action dated Jan. 27, 2009 for U.S. Appl. No. 11/116,952 (7 pgs).

Response to Office Action dated Apr. 27, 2009 for U.S. Appl. No. 11/116,952 (6 pgs.).

* cited by examiner

TUBE SENSOR FOR PENILE TUMESCENCE

TECHNICAL FIELD

The invention relates to implantable medical devices and, more particularly, implantable sensors.

BACKGROUND

Sexual dysfunction of the penis is a common problem afflicting males of all ages, genders, and races. Erectile dysfunction is a serious condition for many men, and it may include a variety of problems. Some of these problems include the inability to create an erection, incomplete erections and brief erectile periods. These conditions may be associated with nervous system disorders and may be caused by aging, injury, or illness.

In some cases, erectile dysfunction can be attributed to improper nerve activity that incompletely stimulates the penis. For example, stimulation from the brain during arousal and sexual activity is responsible for activating an erection. With respect to erectile disorders, the problem may be a lack of sufficient stimulation from the brain or a break in communication of the stimulation. Other disorders may involve dysfunctional parasympathetic function that can be attributed to many factors including illness or injury. Clinical evaluation of erectile dysfunction depends on patient description and possible catheter-based pressure measurements in the clinical setting.

Some methods for treating erectile dysfunction include pharmaceutical treatment and electrical stimulation. Delivery of electrical stimulation to nerves running through the pelvic floor may provide an effective therapy for many patients. For example, an implantable neurostimulator may be provided to deliver electrical stimulation to the pudendal or cavernous nerve to induce an erection.

SUMMARY

The invention is directed to a flexible tube sensor that is implantable to sense penile tumescence, as well as a neurostimulation system and method that make use of such a sensor for alleviation of erectile dysfunction. The sensor includes a thin, flexible tube and a sensing element to detect pressure levels within the tube. The flexible tube may be deployed within the bladder neck or urethra to transduce pressure exerted by the swelling of penile tissue on the urethra as a function of the pressure within the flexible tube. Alternatively, the flexible tube may be deployed within or adjacent to the corpus cavernosa of the penis. In either case, the flexible tube is generally thin and flexible, permitting ready deployment within the penis without significant disruption of sexual or urinary function.

Inadequate penile tumescence during sexual arousal, i.e., erectile dysfunction, may be a result of faulty nervous system function of the sexual organs. The flexible tube sensor may provide short- or long-term monitoring of penile pressure for storage and offline analysis by a clinician. In addition, a flexible tube sensor may provide feedback in a closed-loop neurostimulation system to control and sustain a state of erection during the course of sexual activity.

Neurostimulation therapy is applied to increase blood flow to the penis, thereby promoting tumescence and causing an erection. An implantable neurostimulator may be responsive to penile pressure signals generated by the flexible tube sensor, as described herein, to provide closed-loop neurostimulation therapy to treat erectile dysfunction. In particular, stimulation parameters can be adjusted in response to the penile pressure signals to sustain a state of erection.

In one embodiment, the invention provides an implantable electrical stimulation system comprising an implantable pressure sensor including a flexible tube and a sensing element that senses a pressure level within a penis of a patient based on a pressure level within the tube, and an implantable stimulator that delivers electrical stimulation to the patient based on the sensed pressure level within the penis.

In another embodiment, the invention provides a method comprising sensing a pressure level within a penis of a patient based on a pressure level within a flexible tube placed within the penis, and delivering electrical stimulation to the patient via an implanted stimulator based on the sensed pressure level.

In an additional embodiment, the invention provides an implantable penile tumescence sensor comprising a flexible tube, a sensing element that senses a pressure level within the flexible tube, a fixation mechanism that positions the flexible tube within a penis of a patient, and circuitry that determines a tumescence level within the penis based on the sensed pressure level.

In various embodiments, the invention may provide one or more advantages. For example, the use of a thin, flexible tube sensor permits pressure to be sensed within the narrow, constricted passage of the urethra, or within or adjacent to the corpus cavernosa. In this manner, pressure can be sensed without significantly obstructing or altering the physiological function or the bladder, sexual organs, or urethra.

The flexible tube sensor may be coupled to a larger sensor housing that resides within the bladder or abdomen and houses sensor electronics for transducing a pressure level of the tube. In some embodiments, the sensor housing may reside within the penis itself. The flexible tube sensor permits pressure information to be obtained on a continuous or periodic basis as the patient goes about a daily routine and, more importantly, during the course of sexual activity. In addition, the flexible nature of the tube permits the sensor to be implanted in a variety of locations, constructed in variety of shapes and sizes, and flex with the changing shape of the penis.

The flexible tube sensor may transmit sensed pressure information to an implantable stimulator to permit dynamic control of the therapy delivered by the stimulator on a closed-loop basis. For example, the stimulator may adjust stimulation parameters, such as amplitude, pulse width or pulse rate, in response to the sensed pressure levels. In this manner, the stimulator can respond to changes in sexual activity and maintain penile tumescence at a desired pressure level. Also, with closed-loop stimulation, the stimulator may generate stimulation parameter adjustments that more effectively target erectile function, thereby enhancing stimulation efficacy.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
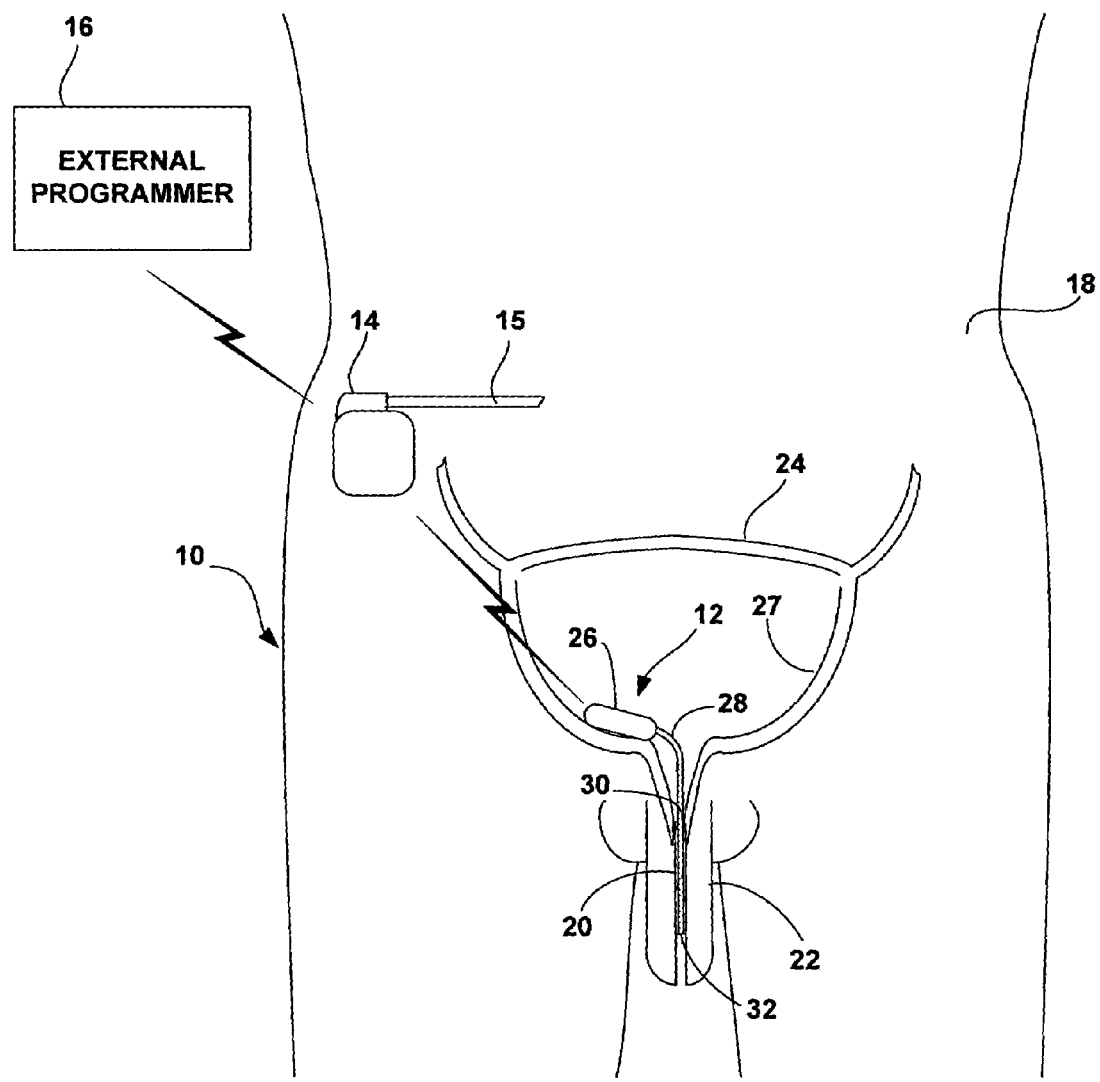
FIG. 1 is a schematic diagram illustrating an implantable stimulation system, incorporating a penile tumescence sensor, for alleviation of sexual dysfunction.

FIG. 1 is a schematic diagram illustrating an implantable stimulation system 10 for alleviation of sexual dysfunction. As shown in FIG. 1, system 10 may include an implantable pressure sensor 12, implantable stimulator 14 and external programmer 16 shown in conjunction with a patient 18. Pressure sensor 12 senses a pressure level of penis 22 on urethra 20 distal to bladder 24, and transmits pressure information based on the sensed pressure level to at least one of stimulator 14 and programmer 16 by wireless telemetry.

The sensed pressure level represents a level of tumescence of penis 22, i.e., a level of blood flow into the penis and a resulting level of engorgement. In this manner, pressure sensor 12 permits the erectile state of penis 22 to be monitored. Sensor 12, stimulator 14 or programmer 16 may record the pressure information. Alternatively, or additionally, stimulator 14 or programmer 16 may generate adjustments to electrical stimulation parameters applied by the stimulator in response to the pressure information, permitting closed loop feedback of erectile state information during the course of sexual activity.

In some embodiments, stimulator 14 or programmer 16 may generate adjustments to parameters in response to pressure information to support delivery of electrical stimulation to support distinct phases of sexual activity, and transition between such phases. For example, based on the pressure information obtained by sensor 12, stimulator 14 or programmer 16 may adjust stimulation parameters to maintain a particular phase of sexual activity, transition from one phase to another, and transition from one phase to a cessation of sexual activity. Examples of distinct phases of sexual activity include arousal, e.g., desire, erection or lubrication, and orgasm or ejaculation. To support distinct phases of sexual activity and progression between phases, sensor 12, stimulator 14, and programmer 16 may be configured to operate in conjunction with stimulation devices and techniques described in U.S. patent application Ser. No. 10/441,784, to Martin Gerber, filed May 19, 2003, entitled "TREATMENT OF SEXUAL DYSFUNCTION BY NEUROSTIMULATION," the entire content of which is incorporated herein by reference.

Figure 2:
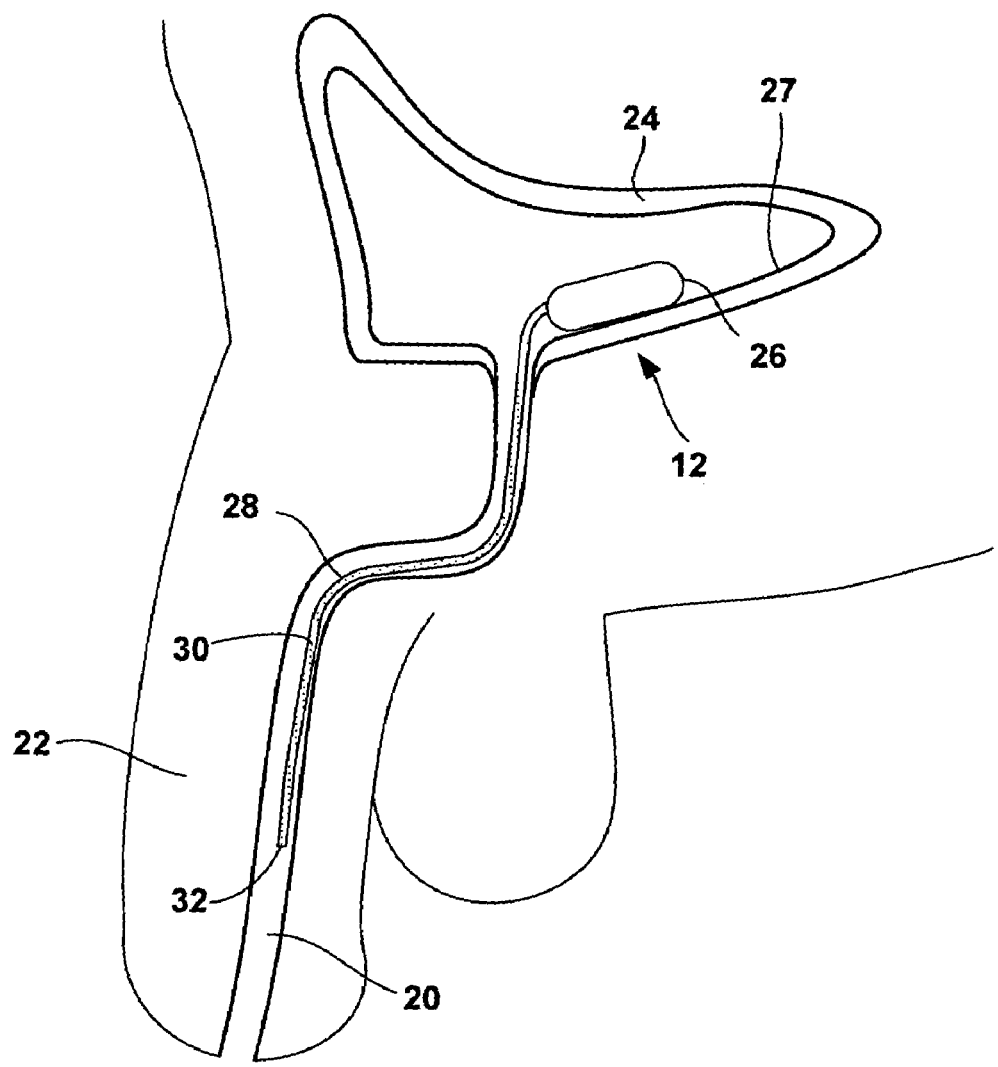
FIG. 2 is an enlarged side view of an implantable pressure sensor with a flexible tube extending through the urethra of a patient.

FIG. 2 is a side view illustrating implantable pressure sensor 12 implanted within urethra 20 and bladder 24. As shown in FIGS. 1 and 2, pressure sensor 12 includes a sensor housing 26 and a flexible tube 28 that extends from the housing. Flexible tube 28 includes a closed end 32 and an open end (not shown in FIG. 1). Sensor housing 26 contains a sensing element (not shown in FIG. 1) adjacent the open end of flexible tube 28. Sensor housing 26 further contains electronics to generate pressure information, and telemetry circuitry for transmission of the information. The sensing element senses the pressure level within flexible tube 28. Flexible tube 28 may contain a fluid, such as a gas or liquid.

As further shown in FIGS. 1 and 2, sensor housing 26 may reside within bladder 24. Sensor housing 26 may be temporarily or permanently attached to an inner wall 27 of bladder 24, such as the mucosal lining, as will be described. Alternatively, housing 26 may be implanted sub-mucosally. Flexible tube 28 extends away from sensor housing 26, out of bladder 24 and through urethra 20. In this manner, flexible tube 28 is positioned to directly sense the pressure level exerted within urethra 20 inside of the shaft of the penis 22. Yet, flexible tube 28 may be sufficiently thin to avoid significant obstruction of urethra 20 or disruption of the function of other urinary or reproductive structures.

As a further alternative, housing 26 may reside outside bladder 24, in which case flexible tube 28 may extend into bladder 24 and through urethra 20 through a hole formed in the bladder. In this case, housing 26 may be surgically or laparoscopically implanted within the abdomen. Tubes 28 may be surgically or laparoscopically guided through a hole in the wall of bladder 24. A cystoscope may be used to grab tube 28 and pull it downward through urethra 20. In some embodiments, housing 26 and its contents may be integrated with stimulator 14, in which case flexible tube 28 extend from the stimulator housing and into bladder 24, much like leads carrying stimulation or sense electrodes.

With further reference to FIG. 1, implantable stimulator 14 includes an electrical lead 15 (partially shown in FIG. 1) carrying one or more electrodes that are placed at a nerve site within the pelvic floor. For example, the electrodes may be positioned to stimulate the prostate parasympathetic nerve, the cavernous nerve, the pudendal nerve, the sacral nerves to support and maintain an erection of penis 22. In particular, electrical stimulation may be applied to increase penile tumescence, i.e., blood flow into the penis 22, that enables the patient to achieve an erection and participate in normal sexual activity. Further, the level of stimulation may be modified based on closed-loop feedback from sensor 12 to maintain the tumescence of penis 22 at target level.

In this manner, implantable stimulator 14 delivers stimulation therapy to the in order to achieve and maintain desired penile tumescence. At predetermined times, or at patient controlled instances, the external programmer 16 may program stimulator 14 to begin stimulation to achieve an erection. Upon the completion of sexual activity or after a predetermined period of time, stimulator 14 may cease stimulation to allow the erection to subside.

During the course of stimulation, stimulator 14 may adjust the stimulation delivered to the patient. For example, adjustment of stimulation parameters may be responsive to pressure information transmitted by implantable pressure sensor 12. External programmer 16 or implantable stimulator 14 may adjust stimulation parameters, such as amplitude, pulse width, and pulse rate, based on pressure information received from implantable sensor 12. In this manner, implantable stimulator 14 adjusts stimulation to either increase or reduce penile tumescence based on the actual pressure level sensed within urethra 20.

Pressure sensor 12 may transmit pressure information periodically, e.g., every few seconds, during the course of sexual activity. Alternatively, each pressure measurement may be obtained by pressure sensor 12 in response to a request from stimulator 14 or programmer. In either case, stimulator 14 or programmer 16 may activate pressure sensor 12, e.g., by wireless telemetry, to commence sensing. In some embodiments, pressure sensor 12 may transmit pressure information when there is an abrupt change in sphincter pressure, e.g., a pressure change that exceeds a predetermined rate threshold, which indicates sexual arousal. In this case, pressure sensor 12 may sense pressure levels at relatively long intervals, and then self-activate sensing at shorter intervals upon detection of the onset of sexual activity.

External programmer 16 may be a small, battery-powered, portable device that may accompany the patient 18 throughout the day or only during sexual activity. Programmer 16 may have a simple user interface, such as a button or keypad, and a display or lights. Patient 18 may initiate an erection, i.e., a voluntary increase in penile tumescence, via the user interface. In particular, in response to a command from the patient 18, programmer 16 may activate stimulator 14 to deliver electrical stimulation therapy. In some embodiments, the length of time for an erection event may be determined by pressing a button a first time to initiate stimulation and a second time when the sexual activity is complete, or by a predetermined length of time permitted by programmer 16 or implantable stimulator 14. In each case, programmer 16 causes implantable stimulator 14 to temporarily stimulate patient 18 to promote penile tumescence.

Implantable stimulator 14 may be constructed with a biocompatible housing, such as titanium or stainless steel, and surgically implanted at a site in patient 18 near the pelvis. The implantation site may be a subcutaneous location in the side of the lower abdomen or the side of the lower back. One or more electrical stimulation leads 15 are connected to implantable stimulator 14 and surgically or percutaneously tunneled to place one or more electrodes carried by a distal end of the lead at a desired nerve site, such as a prostate parasympathetic, pudendal, sacral, or cavernous nerve site.

In the example of FIGS. 1 and 2, sensor housing 26 of implantable pressure sensor 12 is attached to the inner wall 27 of bladder 24. However, the attachment site for sensor housing 26 could be anywhere with access to urethra 20. Also, although a single tube 28 is illustrated for purposes of example, pressure sensor 12 may include multiple tubes or multiple sensors. With a relatively long flexible tube 28, for example, sensor housing 26 could be positioned at a greater distance from the exit of bladder 24.

Also, in some embodiments, sensor housing 26 may be attached within urethra 20, e.g., closer to the section of urethra 20 within penis 22, although attachment of the sensor housing within bladder 24 may be desirable to avoid obstruction of the urethra. In other embodiments, sensor housing 26 could be surgically or laparoscopically implanted outside of bladder 24. In this case, flexible tube 28 may be coupled to the sensor housing 26 and tunneled through a hole in the wall of bladder 24 and into urethra 20, either by introduction of the tube through the urethra and upward into the bladder, or by introduction of the tube into the bladder and downward into the urethra.

Figure 3:
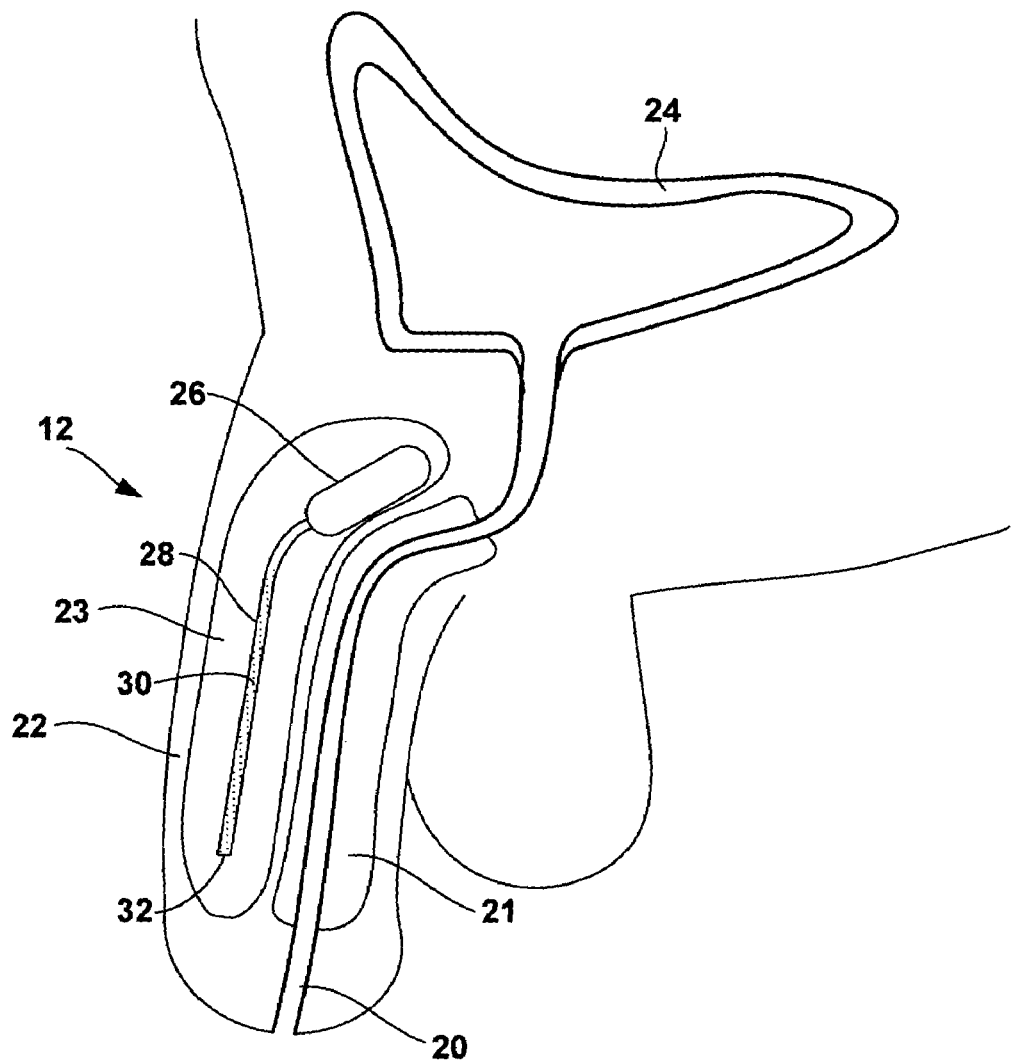
FIG. 3 is an enlarged side view of an implantable pressure sensor with a flexible tube residing within the penis of a patient.

FIG. 3 is an enlarged schematic diagram illustrating the side view of an implantable pressure sensor 12 with a flexible tube 28 residing within the penis 22 of a patient 18. In the example of FIG. 3, sensor 12 and flexible tube 28 are surgically implanted within tissue of penis 22. Some patients may benefit from implantation of sensor 12 and tube 28 within penis 22 when bladder 24 or urethra 20 are not able to carry a device without obstruction or impaired urinary or sexual function. The corpus cavernosa penis 23 and corpus cavernosa urethrae 21 are structures that swell with blood during arousal and erection. Therefore, placement of the sensor within or adjacent to corpus cavernosa penis 23 or corpus cavernosa urethrae 21 may provide accurate sensing of tumescence within penis 22.

As shown in FIG. 3, sensor housing 26 and flexible tube 28 are shown surgically implanted into one of the corpus cavernosa penis 23 segments of penis 22. Sensor housing 26 may simply lie within the tissue or be attached to the outer lining of corpus cavernosa penis 23. Sensor housing 26 may be attached by simple sutures or by any of a variety of fixation mechanisms, which will be described in greater detail herein in the context of attachment of the sensor housing within bladder 24. Once implanted, pressure sensor 12 does not readily move within the tissue. The flexible tube 28 may move with the body of the penis 22 as the penis changes position or expands. Flexible tube 28 may vary in length depending on the size of penis 22 or the placement site of sensor housing 26.

In another embodiment, implantable sensor 12 may be surgically implanted into corpus cavernosum urethrae 21. The corpus cavernosum urethrae 21 of penis 22 surrounds urethra 20 throughout the body of the penis. Placement of the sensor 12 in corpus cavernosum urethrae 21 may enable tumescence sensing while further minimizing the impact of the sensor during sexual activity. In either case, implantation of sensor 12 within the body of penis 22, rather than within urethra 20, may present less risk of obstruction of urine flow.

Figure 4:
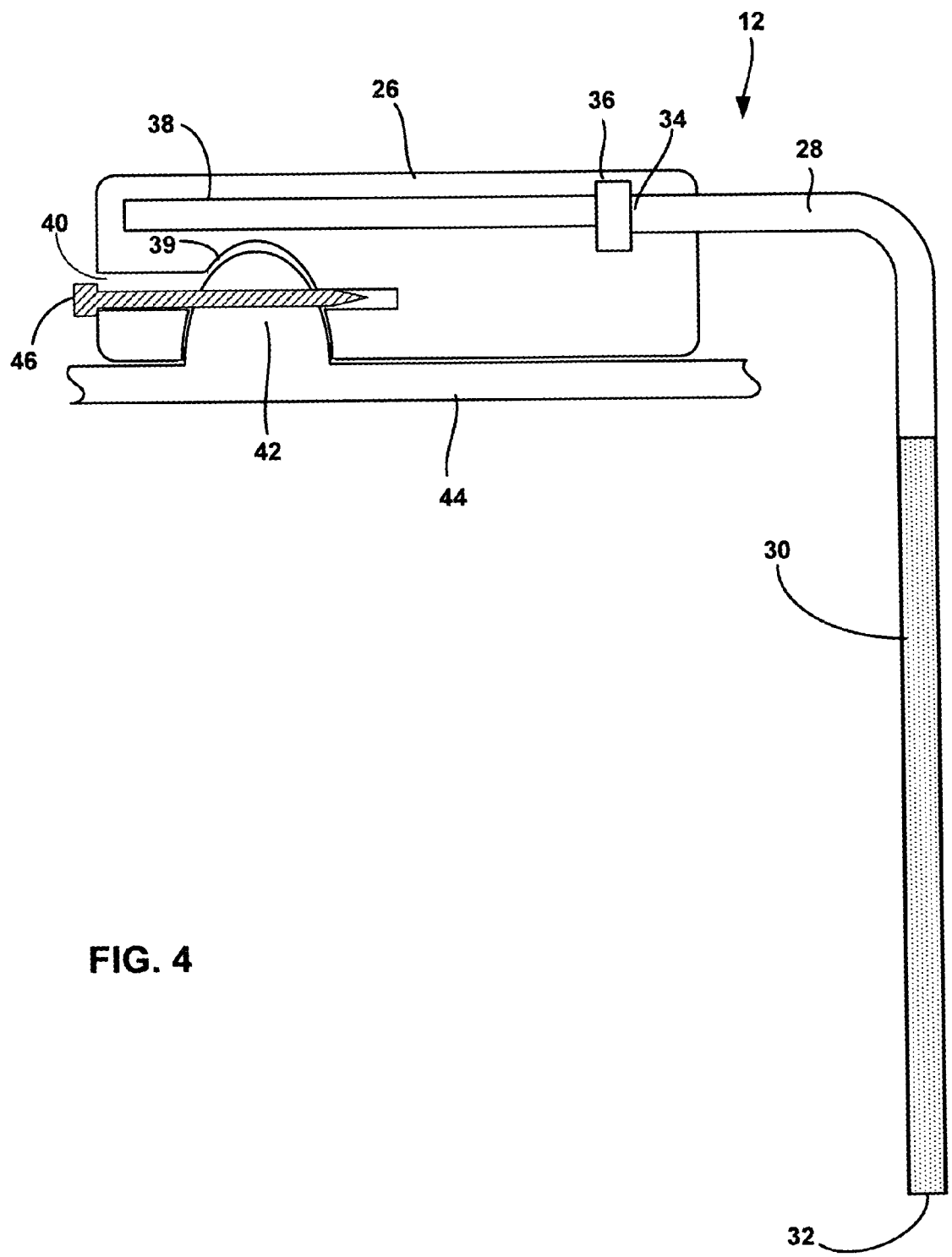
FIG. 4 is an enlarged, cross-sectional side view of the implantable pressure sensor of FIGS. 1 and 2.

FIG. 4 is an enlarged, cross-sectional side view of implantable pressure sensor 12 of FIGS. 1 and 2. As shown in FIG. 4, sensor housing 26 receives an open end 34 of flexible tube 28. A sensing element 36 is mounted within sensor housing 26, at open end 34, to sense a pressure level within fluid tube 28. Sensing element 36 may be coupled to a circuit board 38 within sensor housing 26. Circuit board 38 carries suitable electronics for processing signals generated by sensing element 36. In particular, circuit board 38 may include circuitry that determines a tumescence level within penis 22 based on the sensed pressure level obtained from sensing element 36.

In the example of FIG. 4, flexible tube 28 is filled with a fluid to transduce the pressure on the tube to sensing element 36. Inward deformation of flexible tube 28 causes an elevation in the internal pressure of the tube. Sensing element 36 senses the elevation in pressure at open end 34 of flexible tube 28, and generates a pressure signal that represents the pressure level. Although end 34 is referred to as "open," it is sealed by sensing element 36. Consequently, deformation of flexible tube 28 causes a change in the tube volume, and hence pressure changes in the fluid 30 within the tube.

Flexible tube 28 may be formed from a variety of flexible materials, including polyurethane or silicone. The flexibility of tube 28 permits the tube to conform to contours within urethra 20, or penis 22, and deform in response to changes in penis 22 and pressure exerted on urethra 20. In particular, a rise in penile tumescence results in exertion of pressure inward against the outer wall of urethra 20. In turn, the inner wall of urethra 20 exerts pressure inward against the outer wall of flexible tube 28, causing the wall of the tube to deform and compress inward, providing an indication of penile tumescence.

Sensing element 36 may include a strain gauge sensor, e.g., formed by thin film deposition on a flexible membrane. Circuit board 38 may include processing electronics to process signals generated by sensing element 36, and generate pressure information based on the signals monitoring the pressure level of each tube. In addition, circuit board 38 may include telemetry circuitry for wireless telemetry with stimulator 14, external programmer 16, or both.

Sensing elements 36, in some embodiments, may be constructed as a membrane that carries a resistive strain gauge or piezoelectric element selected to be effective as a pressure transducer. Upon deformation of the membrane, in response to pressure levels within their respective tubes, sensing element 36 produces an electrical signal. When penile pressure increases, the flexible tube 28 deforms and the pressure inside the tube increases. The higher pressure forces the membrane within sensing element 36 to deform, thus producing an electrical signal change and enabling implanted pressure sensor 12 to measure pressure and, indirectly, penile tumescence.

Fluid 30 contained within the tube may be a liquid or gas, or a combination of liquid and gas. For example, flexible tube 28 could be filled with saline, distilled water, oxygen, air or any other biocompatible fluid. Preferably, the fluid 30 within the tubes is generally non-compressible. Fluid 30 tends to exhibit an elevation in pressure as the walls of tube 28 are deformed during engorgement of penis 22. Conversely, fluid 30 exhibits a reduction in pressure as penis 22 relaxes. In each case, the pressure level is transduced by sensing element 36, and can be communicated to stimulator 14, programmer 16, or both for analysis or closed loop control of stimulation parameters Flexible tube 28 may be provided with different dimensions selected for patients having different anatomical dimensions. In particular, implantable pressure sensor 12 may be constructed with a flexible tube 28 having different lengths or diameters. Different tube lengths maybe necessary given the distance between the attachment site of sensor housing 26 and urethra within penis 22, either to ensure that flexible tube 28 reaches the distal urethra or does not extend too far down urethra 20. It may also be important for tube 28 to remain within urethra 20 while the penis is both flaccid and erect. Multiple diameters may also be necessary to allow tube 28 to be placed into both a large or narrow urethra 20. The dimensions may be fixed for a given pressure sensor 12, as a complete assembly. Alternatively, tubes of different sizes may be attached to a pressure sensor housing 26 by a physician prior to implantation.

In general, flexible tube 28 may have a length of less than approximately 9 cm and more preferably less than approximately 7 cm. In some embodiments, flexible tube 28 may have a length of approximately 0.5 cm to 3 cm. The lengths of tube 28 may vary according to the anatomy of the patient. In addition, tube 28 may have an outer diameter in a range of approximately 1 to 3 mm. The wall of tube 28 may be relatively thin to ensure sufficient deformation and conformability, yet thick enough to ensure structural integrity. As an example, the thickness of the wall of tube 28 may be in a range of approximately 0.1 mm to 0.3 mm.

Sensor housing 26 may be made from a biocompatible material such as titanium, stainless steel, or nitinol, or polymeric materials such as silicone or polyurethane. In general, sensor housing 26 contains no external openings, with the exception of the opening to receive flexible tube 28, thereby protecting sensing element 26 and circuit board 38 from the environment within bladder 24. The proximal, open end 34 of flexible tube 28 resides within sensor housing 26 while the distal, closed end 32 resides outside of the sensor housing. The opening in sensor housing 26 that receives open end 34 of flexible tube 28 may be sealed to prevent exposure of interior components.

Attaching implantable pressure sensor 12 to the mucosal lining of bladder 24 may be accomplished in a variety of ways, but preferably is completed in a manner that will not excessively injure bladder 24. Preferably, attachment should cause limited inflammation no adverse physiological modification, such as tissue infection or a loss in structural integrity of bladder 24. However, it is desirable that implantable pressure sensor 12 also be attached securely to the attachment site in order to provide an extended period of measurement without prematurely loosening or detaching from the intended location.

As an example, sensor housing 26 may contain a vacuum cavity 39 that permits a vacuum to be drawn by a vacuum channel 40. The vacuum is created by a deployment device having a vacuum line in communication with vacuum channel 40. The vacuum draws a portion 42 of the mucosal lining 44 of bladder 24 into vacuum cavity 39. Once the portion 42 of mucosal lining 44 is captured within vacuum cavity 39, a fastening pin 46 is driven into the captured tissue to attach sensor housing 26 within bladder 24. Fastening pin 46 may be made from, for example, stainless steel, titanium, nitinol, or a high density polymer. The shaft of pin 46 may be smooth or rough, and the tip may be a sharp point to allow for easy penetration into tissue. Fastening pin 46 may be driven into housing 26 and the portion 42 of mucosal lining 44 under pressure, or upon actuation by a push rod, administered by a deployment device.

In some embodiments, fastening pin 46 may be manufactured from a degradable material that the breaks down over time, e.g. in the presence of urine, to release implantable pressure sensor 12 within a desired time period after attachment. In still another embodiment, implantable pressure sensor 12 may be attached without the use of a penetrating rod but with a spring-loaded clip to pinch trapped mucosal lining 44 within cavity 39. A variety of other attachment mechanisms, such as pins, clips, barbs, sutures, helical screws, surgical adhesives, and the like may be used to attach sensor housing 26 to mucosal lining 44 of bladder 24. Similar attachment mechanisms may be used when implanting sensor 12 within the body of penis 22, e.g., within or adjacent to corpus cavernosa penis 23 and corpus cavernosa urethrae 21.

Figure 5:
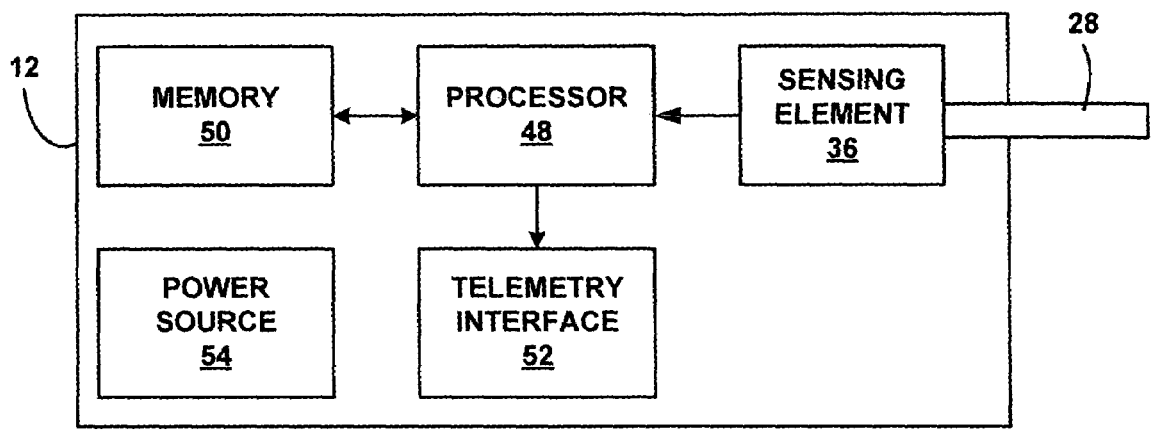
FIG. 5 is functional block diagram illustrating various components of an exemplary implantable pressure sensor.

FIG. 5 is functional block diagram illustrating various components of an exemplary implantable pressure sensor 12. In the example of FIG. 5, implantable pressure sensor 12 includes a sensing element 36, processor 48, memory 50, telemetry interface 52, and power source 54. Sensor 36 transforms pressure levels produced by mechanical deformation from tube 28 into electrical signals representative of penile tumescence. The electrical signals may be amplified, filtered, and otherwise processed as appropriate by electronics within sensor 12. In some embodiments, the signals may be converted to digital values and processed by processor 48 before being saved to memory 50 or sent to implantable stimulator 14 as pressure information via telemetry interface 52.

Memory 50 stores instructions for execution by processor 48 and pressure information generated by sensing element 36. Pressure information may then be sent to implantable stimulator 14 or external programmer 16 for long-term storage and retrieval by a user. Memory 50 may include separate memories for storing instructions and pressure information. In addition, processor 48 and memory 50 may implement loop recorder functionality in which processor 48 overwrites the oldest contents within the memory with new data as storage limits are met.

In some embodiments, sensor 26 may be deployed purely as a diagnostic device to obtain and store penile tumescence measurements over a period of time. In particular, sensor 26 may be used to diagnose a patient's condition in order to determine whether the patient suffers from erectile dysfunction, the degree the dysfunction, and whether electrical stimulation therapy may be desirable. In each case, sensor 26 is entirely ambulatory and requires little or no setup by the patient 18. Instead, sensor 26 simply accompanies patient 18 throughout his daily routine. Loop recorder functionality may be especially desirable for monitoring of penile tumescence over an extended period of time. Following implantation of stimulator 14, sensor 26 may function as both a diagnostic device and a closed loop feedback device for the stimulator.

Processor 48 controls telemetry interface 52 to send pressure information to implantable stimulator 14 or programmer 16 on a continuous basis, at periodic intervals, or upon request from the implantable stimulator or programmer. Wireless telemetry may be accomplished by radio frequency (RF) communication or proximal inductive interaction of pressure sensor 12 with stimulator 14 or programmer 16.

Power source 54 delivers operating power to the components of implantable pressure sensor 12. Power source 54 may include a battery and a power generation circuit to produce the operating power. In some embodiments, the battery may be rechargeable to allow extended operation Recharging may be accomplished through proximal inductive interaction between an external charger and an inductive charging coil within sensor 12. In some embodiments, power requirements may be small enough to allow sensor 12 to utilize patient motion and implement a kinetic energy-scavenging device to trickle charge a rechargeable battery. In other embodiments, traditional batteries may be used for a limited period of time. As a further alternative, an external inductive power supply could transcutaneously power sensor 12 whenever pressure measurements are needed or desired.

Figure 6:
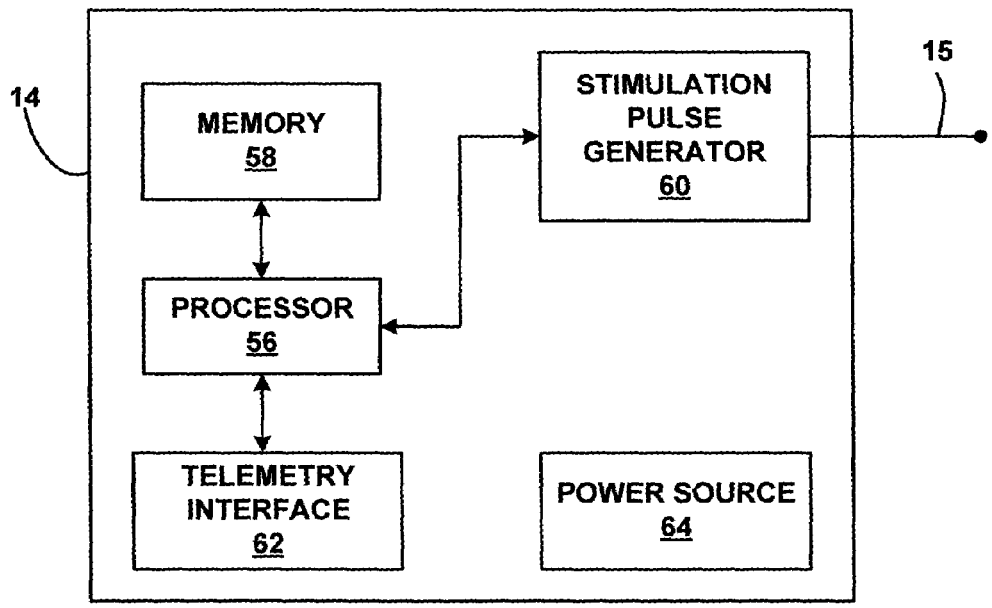
FIG. 6 is a functional block diagram illustrating various components of an implantable stimulator.

FIG. 6 is a functional block diagram illustrating various components of an implantable stimulator 14. In the example of FIG. 6, stimulator 14 includes a processor 56, memory 58, stimulation pulse generator 60, telemetry interface 62, and power source 64. Memory 58 stores instructions for execution by processor 56, stimulation therapy data, and pressure information received from pressure sensor 12 via telemetry interface. Pressure information is received from pressure sensor 12 and may be recorded for long-term storage and retrieval by a user, or adjustment of stimulation parameters, such as amplitude, pulse width or pulse rate. Memory 58 may include a single memory, or separate memories for storing instructions, stimulation parameter sets, and pressure information.

Processor 56 controls stimulation pulse generator 60 to deliver electrical stimulation therapy via one or more leads 15. Processor 56 also controls telemetry interface 62 to send information to stimulator 14, programmer 16, or both, and optionally receive information. Based on pressure information received from sensor 12, processor 56 interprets the information and determines whether any therapy parameter adjustments should be made. For example, processor 56 may compare the pressure level to one or more thresholds, and then take action to adjust stimulation parameters based on the pressure level. Information may be received from sensor 12 on a continuous basis, at periodic intervals, or upon request from stimulator 14 or external programmer 16. Alternatively, or additionally, pressure sensor 12 may transmit pressure information when there is an abrupt change in the pressure level, e.g., at the onset of sexual arousal.

Processor 56 modifies parameter values stored in memory 58 in response to pressure information from sensor 12, either independently or in response to programming changes from external programmer 16. In other words, stimulator 14 may directly control its own parameters in response to information obtained from sensor 12. Alternatively, programmer 16 may direct the parameter adjustments. Stimulation pulse generator 60 provides electrical stimulation according to the stored parameter values via a lead 15 implanted proximate to a nerve, such as a prostate parasympathetic nerve. Processor 56 determines any parameter adjustments based on the pressure information obtained form sensor 12, and loads the adjustments into memory 58 for use in delivery of stimulation.

As an example, if the pressure information indicates an inadequate tumescence pressure during a desired erectile event, processor 56 may increase the amplitude, pulse width or pulse rate of the electrical stimulation applied by stimulation pulse generator 60 to increase stimulation intensity, and thereby increase penile tumescence. If tumescence pressure is adequate, processor 56 may implement a cycle of downward adjustments in stimulation intensity until tumescence pressure becomes inadequate, and then incrementally increase the stimulation upward until tumescence pressure is again adequate. In this way, processor 56 converges toward an optimum level of stimulation. Although processor 56 is generally described in this example as adjusting stimulation parameters, it is noted that the adjustments may be generated by external programmer 16, as mentioned above. Stimulator 14 may deliver stimulation pulses with different parameters for different phases of sexual activity, such as arousal and ejaculation. For a first phase of arousal, stimulator 14 may deliver neurostimulation pulses at a frequency in the range of approximately 50 to 150 Hz, and more preferably approximately 70 to 100 Hz. Each pulse for the first phase may have an amplitude in the range of approximately 1 to 10 volts, and more preferably approximately 2 to 5 volts, and a pulse width in the range of approximately 100 to 400 microseconds, and more preferably approximately 200 to 300 microseconds. The duration of the first phase of neurostimulation may depend on a detected transition to the second phase, which may be indicated by sensed tumescence.

For a second phase of ejaculation, stimulator 14 may deliver neurostimulation pulses at a frequency in the range of approximately 1 to 5 Hz, or in the range of approximately 25 to 35 Hz. Each pulse for the second phase may have an amplitude in the range of approximately 1 to 10 volts, and more preferably approximately 2 to 5 volts, and a pulse width in the range of approximately 200 to 700 microseconds, and more preferably approximately 400 to 500 microseconds.

The adequacy of tumescence pressure is determined by reference to the pressure information obtained from sensor 12. Penile pressure may change due to a variety of factors, such as normal nervous activity or arousal. Hence, for a given set of stimulation parameters, the efficacy of stimulation may vary in terms of tumescence pressure, due to changes in the physiological condition of the patient. For this reason, the continuous or periodic availability of pressure information from implantable sensor 12 is highly desirable in order to maintain an optimal level of stimulation in support of sexual activity.

With the pressure information provided by sensor 12, stimulator 14 is able to respond to changes in penile tumescence with dynamic adjustments in the stimulation parameters delivered to the patient 18. In particular, processor 56 is able to adjust parameters in order to maintain erection of penis 22 and thereby avoid prematurely ceasing sexual activity. In some cases, the adjustment may be nearly instantaneous. If pressure sensor 12 indicates an abrupt change in tumescence pressure, stimulator 14 can quickly respond by more vigorously stimulating one or more selected nerve sites to increase penile tumescence.

In general, if the tumescence of penis 22 is not reaching the target pressure, processor 56 may dynamically increase the level of therapy to be delivered. Conversely, if the tumescence of penis 22 is consistently achieving target pressure, processor 56 may incrementally reduce stimulation, e.g., to conserve power resources.

As in the case of sensor 12, wireless telemetry in stimulator 14 may be accomplished by radio frequency (RF) communication or proximal inductive interaction of pressure stimulator 14 with implantable pressure sensor 12 or external programmer 16. Accordingly, telemetry interface 62 may be similar to telemetry interface 52. Also, power source 64 of stimulator 14 may be constructed somewhat similarly to power source 54. For example, power source 64 may be a rechargeable or non-rechargeable battery, or alternatively take the form of a transcutaneous inductive power interface.

Figure 7:
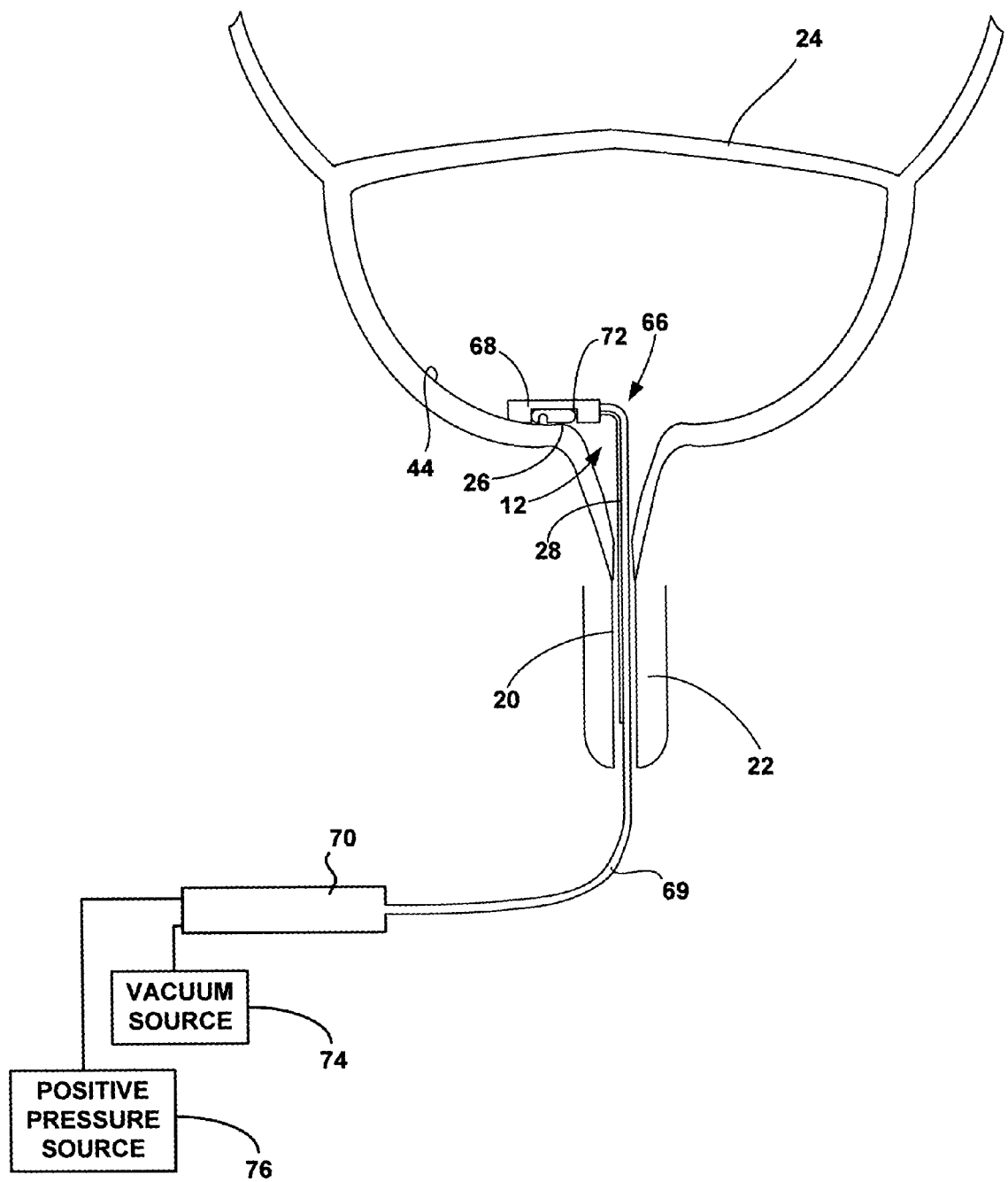
FIG. 7 is a schematic diagram illustrating cystoscopic deployment of an implantable pressure sensor via the urethra.

FIG. 7 is a schematic diagram illustrating cystoscopic deployment of an implantable pressure sensor 12 via the urethra 20 using a deployment device 66. Pressure sensor 12 may be surgically implanted. However, cystoscopic implantation via urethra is generally more desirable in terms of patient trauma, recovery time, and infection risk. In the example of FIG. 7, deployment device 66 includes a distal head 68, a delivery sheath 69 and a control handle 70. Deployment device 66 may be manufactured from disposable materials for single use applications or more durable materials for multiple applications capable of withstanding sterilization between patients.

As shown in FIG. 7, distal head 68 includes a cavity 72 that retains sensor housing 26 of implantable pressure sensor 12 for delivery to a desired attachment site within bladder 24. Sensor housing 26 may be held within cavity 72 by a friction fit, vacuum pressure, or a mechanical attachment. In each case, once distal head 68 reaches the attachment site, sensor housing 26 may be detached. Sheath 69 is attached to distal head 68 and is steerable to navigate urethra 20 and guide the distal head into position. In some embodiments, sheath 69 and distal head 68 may include cystoscopic viewing components to permit visualization of the attachment site. In other cases, external visualization techniques such as ultrasound may be used. Sheath 68 may include one or more steering mechanisms, such as wires, shape memory components, or the like, to permit the distal region adjacent distal head 68 to turn abruptly for access to the mucosal lining of bladder 24.

A control handle 70 is attached to sheath 69 to aid the physician in manually maneuvering deployment device 66 throughout urethra 20 and bladder 24. Control handle 70 may have a one or more controls that enable the physician to contort sheath 69 and allow for deployment device 66 to attach pressure sensor housing 26 to the mucosal lining of bladder 24 and then release the sensor housing to complete implantation. A vacuum source 74 supplies negative pressure to a vacuum line within sheath 69 to draw tissue into the vacuum cavity defined by sensor housing 66. A positive pressure source 76 supplies positive pressure to a drive a fastening pin into the tissue captured in the vacuum cavity.

Deployment device 66 enters patient urethra 20 to deliver pressure sensor 12 and implant it within bladder 24. First, the physician must guide distal head 68 through the opening of urethra 20 in patient 18. Second, distal head 68 continues to glide up urethra 20 and into bladder 24, for access to an appropriate site to attach pressure sensor 12. Using actuators built into control handle 70, sheath 69 is bent to angle distal head 68 into position. Again, sheath 69 may be steered using control wires, shape memory alloys or the like. As pressure sensor 12 is guided into place against the mucosal wall 44 of bladder 24, a physician actuates control handle 70 to attach sensor 12 to mucosal wall 44 and then release the attached sensor. Upon attachment, pressure sensor 12 is implanted within bladder 24 of patient 18 and deployment device 66 is free to exit the bladder. Exemplary methods for attachment and release of sensor 12, including the use of both vacuum pressure and positive pressure, will be described in greater detail below. Although FIG. 7 depicts cystoscopic deployment of pressure sensor 12, surgical or laparoscopic implantation techniques alternatively may be used.

Figure 8:
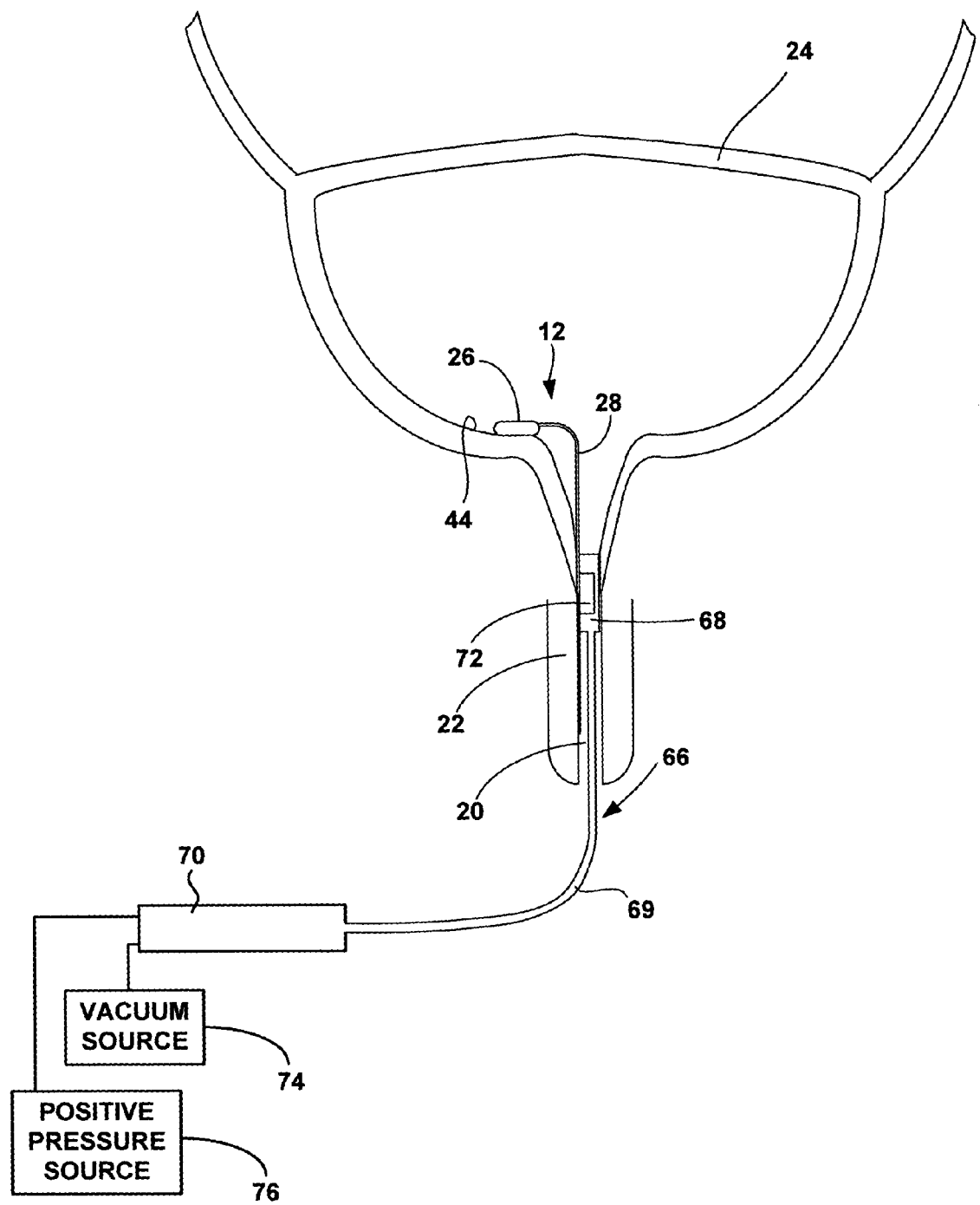
FIG. 8 is a schematic diagram illustrating retraction of a deployment device upon fixation of a pressure sensor within a patient's urinary tract.

FIG. 8 is a schematic diagram illustrating retraction of deployment device 66 upon fixation of pressure sensor 12 within the urinary tract of patient 18. Once the sensor 12 is released, flexible tube 28 remains attached to sensor housing 26. During removal of deployment device 66, tube 28 maintains its position through the neck of bladder 24. As deployment device 66 is removed, tube 28 passes through a guide channel formed in the deployment device. The guide channel ensures that flexible tube 28 remains pinned between distal head 68 and the wall of bladder 24. As distal head 68 slides through urethra 20, however, flexible tube 28 releases from deployment device 66 and is left in place within the urethra in the region of penis 22. Deployment device 66 may then be completely withdrawn past the remainder of urethra 20. In the example of FIG. 8, flexible tube 28 is suspended by device housing 26, which is attached to mucosal wall 44, and is held in place by pressure exerted against the urethral wall by urinary sphincter 22. In other embodiments, tube 28 may be kept in place using other techniques such as actively fixing tube 28 to the side of urethra 20, e.g., with sutures or other anchor mechanisms.

In a preferred embodiment, sheath 69 and distal head 68 may be disposable. Disposable devices that come into contact with patient 18 tissues and fluids greatly decrease the possibility of infection in implantable devices. Control handle 70 does not come into contact with body fluids of patient 18 and may be used for multiple patients. In another embodiment, the entire deployment device 66 may be manufactured out of robust materials intended for multiple uses. The device would then need to be sterilizable between uses. In still a further embodiment, the features of distal head 68 may be incorporated into pressure sensor 12. In this configuration, pressure sensor 12 may be larger in size but would include the necessary elements for attachment within the device. After attachment, the entire sensor would detach from sheath 69, making removal of deployment device 66 easier on patient 18.

After the useful life of implantable pressure sensor 12 is complete or it is no longer needed within patient 18, it can be removed from patient 18 in some manner. As an example, deployment device 66 may be reinserted into patient 18, navigated into bladder 24, and reattached to pressure sensor 12. Deployment device 66 may then be withdrawn from the bladder 24 and urethra 20, explanting sensor 12, including housing 26 and flexible tube 28, from patient 18. In another embodiment, as mentioned with respect to FIG. 3, the attachment method of pressure sensor 12 to bladder 24 may involve degradable materials, such as a biodegradable fixation pin. After a certain period of time exposed to urine in the bladder 24, the fixation material may structurally degrade and allow pressure sensor 12 to be released from the mucosal wall 44 of bladder 24. In some embodiments, sensor 12 may be sized sufficiently small to follow urine out of the bladder, urethra, and body during an urination event. In other embodiments, sensor housing 26 or tube 28 may carry a suture-like loop that can be hooked by a catheter with a hooking element to withdraw the entire assembly from patient 18 via urethra 20. In still further embodiments, such a loop may be long enough to extend out of the urethra, so that the loop can be grabbed with an external device or the human hand to pull the sensor 12 out of the patient.

Figure 9:
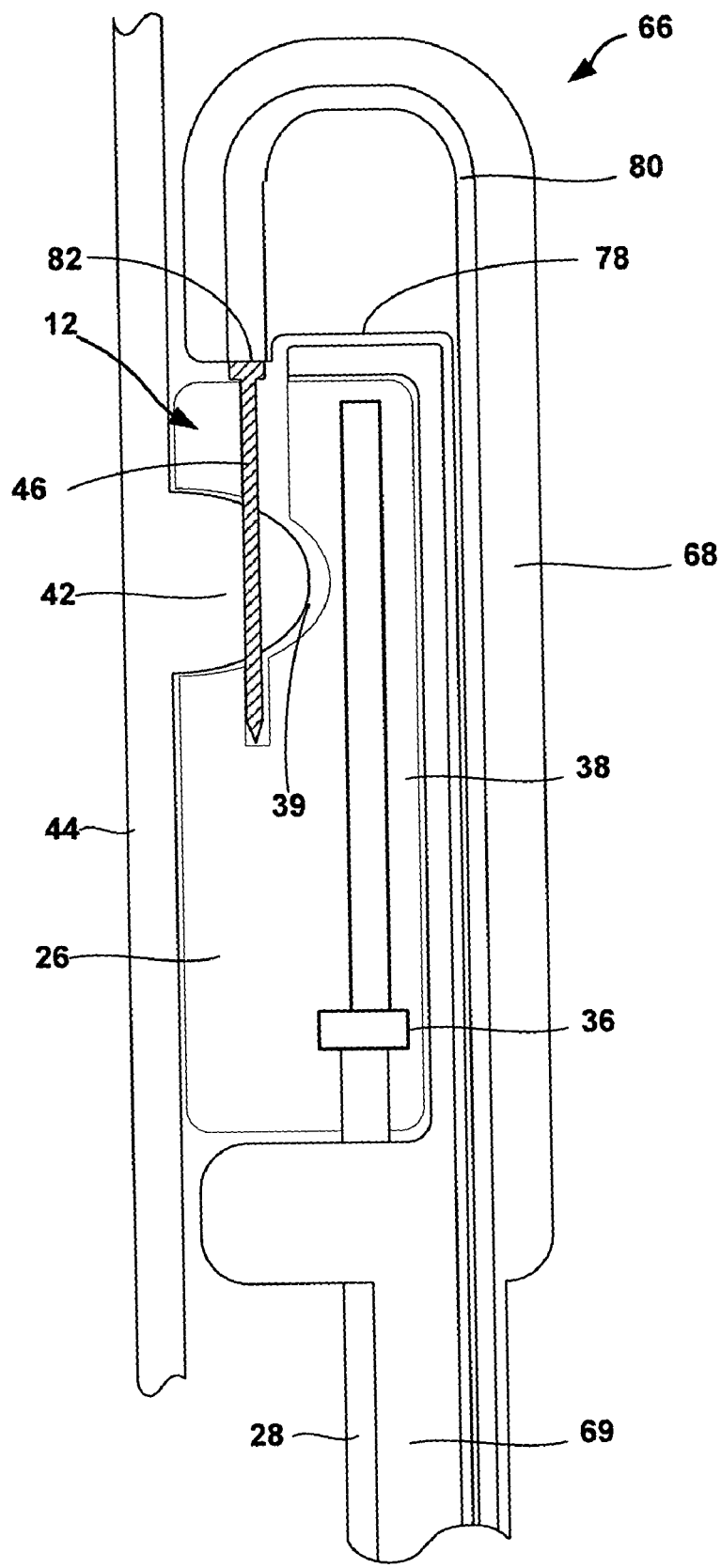
FIG. 9 is a cross-sectional side view of a distal end of a deployment device during deployment and fixation of a pressure sensor.

FIG. 9 is a cross-sectional side view of distal head 68 of deployment device 66 during deployment and fixation of pressure sensor 12. In the example of FIG. 9, distal head 68 includes a vacuum line 78 and a positive pressure line 80. Vacuum line 78 is coupled to vacuum source 74 via a tube or lumen extending along the length of sheath 69. Similarly, positive pressure line 80 is coupled to positive pressure source 76 via a tube or lumen extending along the length of sheath 69. Vacuum line 78 is in fluid communication with vacuum cavity 39, and permits the physician to draw a vacuum and thereby capture a portion 42 of mucosal lining 44 within the vacuum cavity. Although vacuum line 78 is shown as being coupled laterally to vacuum cavity 39, the vacuum line could access the vacuum cavity from another direction, such as the top of the vacuum cavity. Positive pressure line 80 permits the physician to apply a pulse of high pressure fluid, such as a liquid or a gas, to drive fixation pin 46 into sensor housing 26 and through the portion 42 of mucosal lining 44. Pin 46 thereby fixes sensor housing 26 to mucosal lining 44. In some embodiments, a membrane mounted over an opening of positive pressure line 80 may be punctured by pin 46.

Flexible tube 28 resides within a channel of sheath 69 prior to detachment or sensor 12 from distal head 68. Once fixation pin 46 attaches sensor 12 to bladder 24, vacuum line 78 is no longer needed. However, in some embodiments, vacuum line 78 may be used to detach pressure sensor 12 from distal head 68 of deployment device 66. By terminating vacuum pressure, or briefly applying positive pressure through vacuum line 78, for example, head 68 may separate from sensor 12 due to the force of the air pressure. In this manner, vacuum line 78 may aid in detachment of sensor 12 prior to withdrawal of deployment device 66.

As described previously in FIG. 4, fixation pin 46 punctures mucosal lining 44 for fixation of sensor 12. While the force of this fixation may vary with patient 18, deployment device 66 provides adequate force for delivery of pin 46. In an exemplary embodiment, positive pressure line 80 is completely sealed and filled with a biocompatible fluid, such as water, saline solution or air. Sealing the end of positive pressure line 80 is a head 82 on fixation pin 46. Head 82 is generally able to move within positive pressure line 80 much like a piston. Force to push fixation pin 46 through the portion 42 of mucosal lining 44 captured in vacuum cavity 39 is created by application of a pulse of increased fluid pressure within positive pressure line 80. For example, the physician may control positive pressure source 76 via control handle 70. This simple delivery method may provide high levels of force, allow multiple curves and bends in sheath 69, and enable a positive pressure line 80 of many shapes and sizes. In some embodiments, a membrane sealing line 80 may be punctured by pin 46.

In an alternative embodiment, a flexible, but generally incompressible, wire may placed within positive pressure line 80 and used to force fixation pin 46 through the captured portion 42 of mucosal lining 44. This wire presents compressive force from control handle 70 directly to the head 82 of fixation nail 46. This method may eliminate any safety risk of pressurized fluids entering patient 18 or, in some embodiments, permit retraction of pin 46 after an unsuccessful fixation attempt. The flexible wire may be attached to pin 46 and pulled back to remove the pin from capture mucosal tissue 42. The flexible wire may be sheared from fixation nail 46 for detachment purposes as distal head 68 releases sensor 12. This detachment may be facilitated by a shearing element or low shear stress of the wire.

In FIG. 9, deployment device 66 illustrates flexible tube 28 on the same end of housing 26 as sheath 69, while the fixation structures are located in the opposite, or distal end of distal head 68. In some embodiments, it may be necessary for pressure sensor 12 to be deployed with tube 28 located at the distal end of head 68 and the fixation structures located near sheath 69. In still other embodiments, the fixation structures and tube 28 may be located on the same end of pressure sensor 12.

In some embodiments, deployment device 66 may include a small endoscopic camera in the distal head 68. The camera may enable the physician to better guide deployment device 66 through urethra 20 and to a desired attachment location of bladder 24 in less time with more accuracy. Images may be displayed using video fed to a display monitor.

Figure 10:
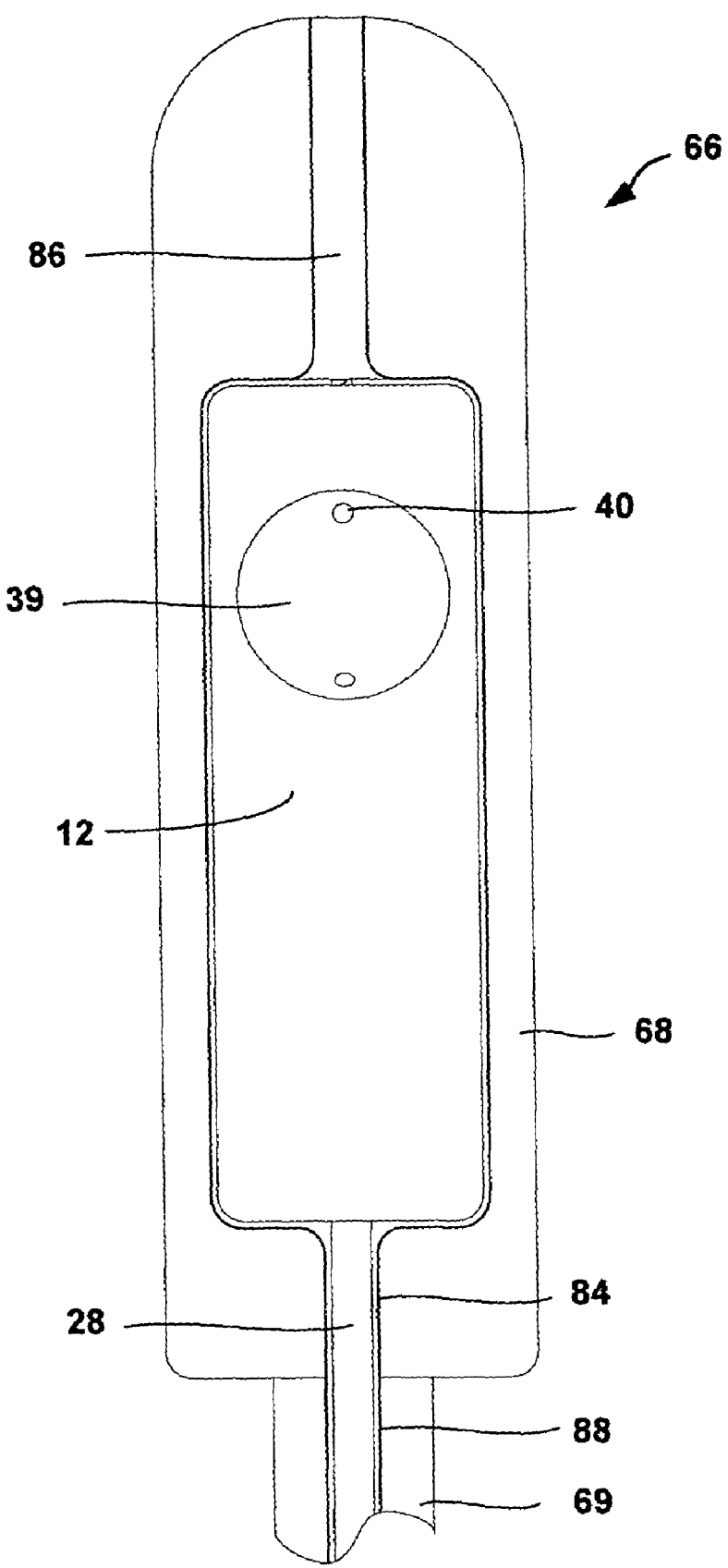
FIG. 10 is a cross-sectional bottom view of the deployment device of FIG. 10 before attachment of the pressure sensor.

FIG. 10 is a cross-sectional bottom view of the deployment device 66 of FIG. 9 before attachment of pressure sensor 12. As shown in FIG. 10, distal head 68 includes proximal tube channel 84 to accommodate flexible tube 28 during placement of sensor 12 and distal tube channel 86 to accommodate the flexible tube during retraction of deployment device 66. In addition, sheath 69 includes a sheath channel 88 to accommodate flexible tube 28. Channels 84, 86, 88 serve to retain tube 28 during delivery of sensor 12 to an attachment site.

Distal head 68 is rounded on both sides at the distal end to permit easier entry of deployment device into areas of patient 18. Head 68 may also be lubricated before delivery to facilitate ease of navigation. On the proximal end of head 68, proximal tube channel 84 runs through the head for unimpeded removal of tube 28 during detachment of pressure sensor 12. This channel may be U-shaped, e.g. closed on 3 sides. In some embodiments, proximal tube channel 84 may be an enclosed hole in which tube 28 resides and glides through upon deployment device 30 removal.

Sheath channel 88 is formed within sheath 69 to allow tube 28 to stay in place during delivery of pressure sensor 12. In this embodiment, tube 28 is only partially retained within channel 88. In some embodiments, sheath channel 88 may be deeper to allow tube 28 to lie completely within sheath 69, whereas others may include a completely enclosed channel that tube 28 must glide out of after attachment.

Distal channel 86 in distal end of head housing 68 is not used by tube 28 before attachment. The purpose of this open channel is to allow tube 28 to glide through it while head 68 is removed from bladder 24. As head 68 slides back past pressure sensor 12, tube 28 will slide through channel 86 and head housing 68 will keep tube 28 between the wall of bladder 24 and head 68 until head 68 has been removed beyond sphincter 22. Tube 28 may then be ensured correct placing through sphincter 22.

Some embodiments of tube 28 include multiple length and diameter combinations which would lead to modifications in channels 84, 86 and 88. These channels herein may be of different diameters or lengths to properly house tube 28. One embodiment may include flexible housing channels to accommodate a wide variety of tube 28 dimensions. Further embodiments of deployment device 30 may contain modified channel locations in head housing 68. These locations may be needed to place tube 28 from different locations, particularly if fixing implantable sensor 12 at different sites within bladder 24 or urethra 20.

Figure 11:
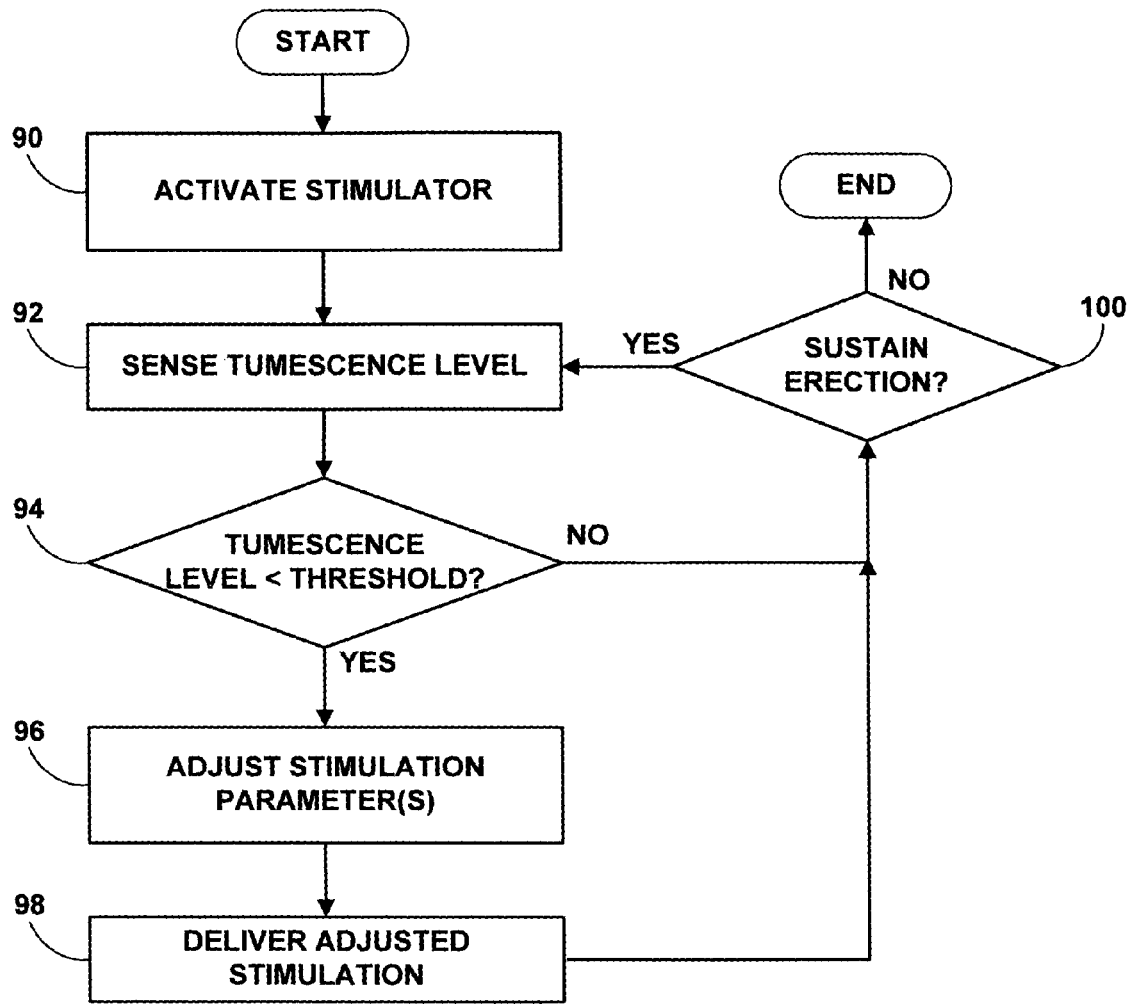
FIG. 11 is a flow chart illustrating a technique for delivery of stimulation therapy to alleviate sexual dysfunction based on closed loop feedback from an implantable pressure sensor.

FIG. 11 is a flow chart illustrating a technique for delivery of stimulation therapy based on closed loop feedback from an implantable pressure sensor. In the example of FIG. 11, implantable stimulator 14 makes use of information obtained from implantable pressure sensor 12 and external programmer 16. A patient 18 activates stimulator (90) by entering a command via a user interface associated with external programmer 16. The command indicates that the patient would like to commence sexual activity. In response to the command, programmer 16 activates stimulator 14 (90) to deliver stimulation therapy.

During the course of stimulation therapy, sensor 12 senses the tumescence level of penis 22 (92), and transmits information indicative of the tumescence level to stimulator 14, programmer 16 or both. The tumescence level correlates with a pressure level sensed by sensor 12, either within urethra 20 or within the body of penis 22. If stimulator 14 or programmer 16 determines that the tumescence level is below an applicable threshold (94), indicating an inadequate erectile state, one or more stimulation parameters are adjusted (96) to provide more vigorous stimulation. The adjustment may be made directly by stimulator 14 or in response to an adjustment command or reprogramming by programmer 16.

Upon delivery of the adjusted stimulation (98), stimulator 14 or programmer 16 determines whether the patient 18 wants to sustain the erection (100), or whether sexual activity has terminated. Patient 18 may terminate sexual activity by entry of a command via a user interface associated with programmer 16. If sustained erection is desired, the process continues with tumescence sensing (92), threshold comparison (94), adjustment of stimulation parameters (96) and delivery of adjusted stimulation (98).

In some embodiments, as mentioned previously, pressure sensor 12 may be used exclusively for monitoring pressure without providing feedback for stimulation therapy. In this case, pressure sensor 12 simply collects data and either stores it locally, or sends it to an external programmer. Pressure may be measured continuously, intermittently or at the request of external programmer 16. These embodiments may be used for disease diagnosis or condition monitoring and may allow a patient to avoid frequent clinic visits and uncomfortable procedures while acquiring more extensive and more accurate pressure data during sexual activity.

Although the invention has been generally described in conjunction with implantable neurostimulation devices, a tube-based tumescence sensor 12 may also be used with other implantable medical devices, implantable drug delivery devices, which may be configured to treat sexual dysfunction. In particular, tumescence levels sensed by a pressure sensor 12 may be used to trigger and control delivery of any of a variety of drugs capable of achieving arousal in a male or female patient. Prostaglandin, Alprostdil, Tadalafil, Sildenafil, Vardenfil are examples of drugs that could be infused, e.g., by intracavernous injection, to elicit an erection in a male patient. Approximate dosages for some of the above drugs are: Alprostdil—10 to 250 micrograms, Sildenafil—10 to 250 micrograms, and Apormorphine—10 to 250 micrograms. The tumescence levels obtained by sensor 12 may be used to trigger drug delivery, control the rate of delivery of the drug, or control the overall amount of drug delivered to the patient, e.g., to achieve and maintain an erection during a first phase of sexual activity. A suitable drug delivery system is described in the aforementioned pending application to Gerber.

Various embodiments of the described invention may include processors that are realized by microprocessors, Application-Specific Integrated Circuits (ASIC), Field-Programmable Gate Array (FPGA), or other equivalent integrated or discrete logic circuitry. The processor may also utilize several different types of storage methods to hold computer-readable instructions for the device operation and data storage. These memory or storage media may include a type of hard disk, random access memory (RAM), or flash memory, e.g. Compact Flash or Smart Media. Each storage option may be chosen depending on the embodiment of the invention. While the implantable stimulator and implantable pressure sensor may contain permanent memory, the patient or clinician programmer may contain a more portable removable memory type to enable easy data transfer for offline data analysis.

Many embodiments of the invention have been described. Various modifications may be made without departing from the scope of the claims. These and other embodiments are within the scope of the following claims.

The invention claimed is:

1. An implantable electrical stimulation system comprising:
    an implantable pressure sensor including a housing, an elongated, flexible tube coupled to the housing, and a sensing element within the housing that senses a pressure level within a penis of a patient as indicated by a pressure level within the tube,
    wherein the implantable pressure sensor includes a fixation mechanism positioned to attach the housing to an inner wall of a bladder of the patient, and
    wherein the elongated, flexible tube is configured to conform to a changing shape and tumescence of the penis; and
    an implantable stimulator that delivers electrical stimulation to the patient based on the sensed pressure level within the penis.

2. The system of claim 1, wherein the flexible tube includes a closed end and an open end, and the sensing element is disposed at the open end.

3. The system of claim 1, wherein the sensing element includes a strain gauge sensor.

4. The system of claim 1, wherein the flexible tube contains a fluid.

5. The system of claim 1, wherein the flexible tube has a length of less than approximately 7 cm and an outer diameter of approximately 1 to 3 mm.

6. The system of claim 1, wherein the fixation mechanism positions the flexible tube within a urethra within the patient.

7. The system of claim 1, wherein the implantable sensor includes a telemetry circuit that transmits information by wireless telemetry based on the sensed pressure level.

8. The system of claim 7, wherein the telemetry circuit transmits the information to the implantable stimulator, the implantable stimulator adjusting one or more parameters of the electrical stimulation based on the transmitted information.

9. The system of claim 7, further comprising an external programmer to adjust stimulation parameters associated with the electrical stimulation delivered by the implantable stimulator, wherein the telemetry circuit transmits the information to the external programmer.

10. The system of claim 1, wherein the implantable stimulator includes a lead carrying one or more electrodes to deliver electrical stimulation to a nerve site that stimulates an erection of the penis.

11. The system of claim 1, wherein the flexible tube has a length of at least 0.5 cm.

12. A method comprising:
    sensing a pressure level within a penis of a patient with an elongated, flexible tube placed within the penis, wherein the pressure level within the penis is indicated by a pressure level within the tube, wherein the elongated, flexible tube is configured to conform to a changing shape and tumescence of the penis, and wherein the flexible tube extends from a sensor housing;
    fixing the sensor housing within a bladder of the patient;
    positioning the flexible tube proximate a urethra within the patient; and delivering electrical stimulation to the patient via an implanted stimulator based on the sensed pressure level.

13. The method of claim 12, wherein the fixation mechanism positions the flexible tube within the urethra of the patient.

14. The method of claim 12, wherein the flexible tube is placed within a corpus cavernosum of the penis.

15. The method of claim 12, wherein the flexible tube includes a closed end and an open end, and sensing a pressure level includes sensing the pressure level via a sensing element disposed at the open end of the flexible tube.

16. The method of claim 15, wherein the sensing element includes a strain gauge sensor.

17. The method of claim 12, wherein the flexible tube contains a fluid.

18. The method of claim 12, wherein the flexible tube has a length of less than approximately 7 cm and an outer diameter of approximately 1 to 3 mm.

19. The method of claim 12, further comprising transmitting information based on the sensed pressure level to the stimulator by wireless telemetry, and adjusting one or more parameters of the electrical stimulation based on the transmitted information.

20. The method of claim 12, further comprising transmitting information based on the sensed pressure level to an external programmer by wireless telemetry, wherein the programmer controls the stimulator to adjust one or more parameters of the electrical stimulation based on the transmitted information.

21. The method of claim 12, wherein the stimulator includes an implanted lead carrying one or more electrodes to deliver electrical stimulation to a nerve site that stimulates an erection of the penis.

22. An implantable electrical stimulation system comprising:
   an implantable pressure sensor including a housing, an elongated, flexible tube coupled to the housing, and a sensing element within the housing that senses a pressure level within a penis of a patient as indicated by a pressure level within the tube; and
   an implantable stimulator that delivers electrical stimulation to the patient based on the sensed pressure level within the penis,
   wherein the elongated, flexible tube is configured to conform to a changing shape and tumescence of the penis,
   wherein the elongated, flexible tube has a length of at least 0.5 cm,
   wherein the implantable pressure sensor includes a fixation mechanism positioned to attach the housing to an inner wall of a bladder of the patient,
   wherein the fixation mechanism is coupled to the housing of the implantable pressure sensor, and
   wherein the elongated, flexible tube is configured to extend from the housing into a urethra of the patient when the housing is attached to the inner wall of the bladder of the patient.

* * * * *